(12) United States Patent
Smith et al.

(10) Patent No.: US 12,171,615 B2
(45) Date of Patent: *Dec. 24, 2024

(54) SYSTEMS FOR MULTIMODAL REAL-TIME IMAGING FOR BIOPSIES AND RELATED METHODS

(71) Applicants: Arizona Board of Regents on behalf of Arizona State University, Scottsdale, AZ (US); Joel Barkley, Tempe, AZ (US)

(72) Inventors: Barbara Smith, Tempe, AZ (US); Joel Barkley, Tempe, AZ (US); Christopher Miranda, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 112 days.

This patent is subject to a terminal disclaimer.

(21) Appl. No.: 17/329,649

(22) Filed: May 25, 2021

(65) Prior Publication Data

US 2021/0275140 A1    Sep. 9, 2021

Related U.S. Application Data

(62) Division of application No. 15/631,672, filed on Jun. 23, 2017, now Pat. No. 11,045,169.

(Continued)

(51) Int. Cl.
*A61B 8/00* (2006.01)
*A61B 5/00* (2006.01)

(Continued)

(52) U.S. Cl.
CPC .......... *A61B 8/4416* (2013.01); *A61B 5/0035* (2013.01); *A61B 5/0059* (2013.01); *A61B 5/0084* (2013.01); *A61B 5/0095* (2013.01); *A61B 8/085* (2013.01); *A61B 8/4245* (2013.01); *A61B 8/4483* (2013.01); *A61B 8/466* (2013.01); *A61B 10/0291* (2013.01);

(Continued)

(58) Field of Classification Search
CPC ... A61B 5/0095; A61B 5/0059; A61B 5/0084; A61B 8/4416; A61B 5/0035; A61B 8/4245

See application file for complete search history.

(56) References Cited

U.S. PATENT DOCUMENTS 5,769,086 A  *  6/1998  Ritchart ............. A61B 10/0275
                                                           600/566
2008/0091104 A1 *  4/2008  Abraham ............... A61B 8/582
                                                           600/439

(Continued)

FOREIGN PATENT DOCUMENTS

WO      WO-9903399 A1 *  1/1999  ......... A61B 17/4241

*Primary Examiner* — Angela M Hoffa
*Assistant Examiner* — Younhee Choi
(74) *Attorney, Agent, or Firm* — Riverside Law LLP

(57) ABSTRACT

A device comprises a cannula having a first end, a second end, and a channel between the first end and the second end; an imaging probe couplable to the first end of the cannula, where the imaging probe includes: a transducer, and a reflective surface; and a biopsy device coupled to the cannula, where the biopsy device is configured to collect a tissue sample from an organ of a patient.

18 Claims, 2 Drawing Sheets

Related U.S. Application Data

(60) Provisional application No. 62/354,389, filed on Jun. 24, 2016.

(51) Int. Cl.
  *A61B 8/08* (2006.01)
  *A61B 10/02* (2006.01)
  *A61B 10/04* (2006.01)
  *G02B 23/24* (2006.01)

(52) U.S. Cl.
  CPC .......... *A61B 10/04* (2013.01); *G02B 23/2423* (2013.01); *G02B 23/2461* (2013.01); *G02B 23/2484* (2013.01); *A61B 5/6847* (2013.01); *A61B 8/462* (2013.01)

(56) References Cited

U.S. PATENT DOCUMENTS

| | | | |
|---|---|---|---|
| 2011/0098572 A1* | 4/2011 | Chen | A61B 5/0062 600/463 |
| 2016/0242650 A1* | 8/2016 | Chen | A61B 5/0035 |
| 2019/0021598 A1* | 1/2019 | Eom | A61B 5/0095 |
| 2019/0046159 A1* | 2/2019 | Smith | A61B 1/04 |

* cited by examiner

SYSTEMS FOR MULTIMODAL REAL-TIME IMAGING FOR BIOPSIES AND RELATED METHODS

CROSS-REFERENCE TO RELATED APPLICATIONS

This application is a divisional of U.S. patent application Ser. No. 15/631,672, filed Jun. 23, 2017, which claims the benefit of priority to U.S. Provisional Application No. 62/354,389, filed Jun. 24, 2016, each of which is incorporated herein by reference in its entirety.

BACKGROUND OF THE INVENTION

1. Field of the Invention

The present invention relates generally to devices for multimodal imaging and more specifically, but not by way of limitation, to devices and related methods of combined photoacoustic and ultrasound imaging with real-time data processing and image reconstruction.

2. Description of Related Art

Traditionally, in the United States, women who enter a clinic with abnormal uterine bleeding—regardless of, shape, color, economic standing, history or ethnicity—are considered to have endometrial cancer, until proven otherwise. Current methods of diagnosis require a combination of imaging and biopsy tests to be performed within a series of multiple clinical visits. Typical diagnostic tests used to rule out endometrial cancer include: i) transvaginal and/or pelvic ultrasound, ii) endometrial biopsy, iii) hysteroscopy, and iv) D&C (dilation and curettage) testing. This succession of painful, expensive, and time-consuming tests fail to meet the needs of the physician and the patient. For example, transvaginal and/or pelvic ultrasounds, endometrial biopsies, and hysteroscopies may render inconclusive results. D&C testing may be considered invasive.

Thus, there remains a need for a system providing more efficient, accurate, and cost-effective imaging and biopsy collection, which may be used in screening for endometrial cancer.

SUMMARY OF THE INVENTION

Some embodiments of the present disclosure include combined photoacoustic and ultrasound imaging capabilities with real-time data processing and image reconstruction.

Some embodiments of the present systems include a motor external relative to a patient configured to move an insertion device for full organ imaging, where the motor may return the insertion device to a specified location in a patient for a (e.g., biopsy) sample collection.

Some embodiments of the present disclosure include a device comprising: a cannula having a first end, a second end, and a channel between the first end and the second end; an imaging probe couplable to the first end of the cannula, where the imaging probe includes: a transducer, and a reflective surface; and a biopsy device coupled to the cannula, where the biopsy device is configured to collect a tissue sample within a patient.

In some embodiments of the present disclosure, the transducer may be at least partially aligned with a first aperture in the imaging probe and the reflective surface may be at least partially aligned with a second aperture in the imaging probe.

In some embodiments of the present disclosure, the first aperture and the second aperture are axially aligned in the imaging probe.

In some embodiments of the present disclosure, the device includes a first transmission line configured to extend from the transducer toward the second end of the cannula.

In some embodiments of the present disclosure, the device includes a second transmission line configured to extend from proximate the reflective surface toward the second end of the cannula.

In some embodiments of the present disclosure, the biopsy device is rotatably fixed relative to the cannula.

In some embodiments of the present disclosure, the device is configured to capture at least an optical image, an ultrasound image, and/or a photoacoustic image.

In some embodiments of the present disclosure, the mapped image provides a three-dimensional mapping of at least one of tissue and vasculature of an organ and/or location of a patient.

Some embodiments of the present systems comprise: a device configured to be insertable into a patient, where the device includes: a cannula having a first end, a second end, and a channel between the first end and the second end, an imaging probe couplable to the first end of the cannula, where the imaging probe includes: a transducer, and a reflective surface; a biopsy device coupled to the cannula, where the biopsy device is configured to collect a tissue sample from the patient; a laser configured to emit a light signal using the reflective surface; a pulser configured to actuate transducer such that the transducer emits an ultrasound signal; a computer configured to construct an image of the organ in real time based on an ultrasound return signal and/or a photoacoustic signal received by the transducer in response to the ultrasound signal and the light signal, respectively; and an actuator coupled to the device and configured to automatically linearly and/or rotationally move the device to a location of interest in the organ based on the ultrasound return signal and/or the photoacoustic signal.

In some embodiments of the present systems, the actuator includes a rotary motor and a linear actuator.

Some embodiments of the present systems further comprise: a laser; a fiber optic alignment stage configured to direct the light signal emitted by the laser toward the reflective surface; a transducer configures to receive an acoustic signal; a receiver configured to receive a signal from the transducer; an amplifier configured to amplify the signal received by receiver; and a data acquisition system configured to receive a signal from the amplifier.

Some embodiments of the present systems further comprise: a position control device configured to direct the actuator to move the device to the location of interest.

In some embodiments of the present systems, the system is configured to capture at least an optical image, an ultrasound image, and/or a photoacoustic image.

In some embodiments of the present systems, the actuator is configured to be disposed externally relative to the organ of the patient.

In some embodiments of the present systems, the image of a region of interest of the patient comprises at least one of an optical image, an ultrasound image, and/or a photoacoustic image.

In some embodiments of the present systems, the image provides a three-dimensional mapping of at least one of tissue and vasculature of the patient, for example, of an organ of a patient.

Some embodiments of the present methods comprise: inserting a device into an organ of a patient, where the device includes: a cannula having a first end, a second end, and a channel between the first end and the second end, an imaging probe couplable to the first end of the cannula, where the imaging probe includes: a transducer, and a reflective surface; a biopsy device coupled to the cannula, where the biopsy device is configured to collect a tissue sample from the organ of the patient; emitting an ultrasound signal using the transducer; emitting a light signal using the reflective surface; receiving an ultrasound return signal and/or a photoacoustic signal in response to emitting the ultrasound signal and the light signal, respectively; forming an image of the organ in real time while receiving the ultrasound return signal and/or the photoacoustic signal; and automatically moving the imaging probe to a location of interest in the organ based on the ultrasound return signal and/or the photoacoustic signal.

Some embodiments of the present methods further comprise: collecting a controlled sample of a tissue of the organ after moving the imaging probe to the location of interest.

In some embodiments of the present methods, the imaging probe is moved while the ultrasound signal and the light signal are emitted.

In some embodiments of the present methods, forming the image includes providing a three-dimensional mapping of at least one of tissue and vasculature of a region of interest of the patient. In particular embodiments this might include mapping an entire organ from inside the organ.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the term "substantially" may be substituted with "within [a percentage] of" what is specified, where the percentage includes. 1, 1, 5, and 10 percent.

Further, a device or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), and "include" (and any form of include, such as "includes" and "including") are open-ended linking verbs. As a result, an apparatus that "comprises," "has," or "includes" one or more elements possesses those one or more elements, but is not limited to possessing only those elements. Likewise, a method that "comprises," "has," or "includes" one or more steps possesses those one or more steps, but is not limited to possessing only those one or more steps.

Any embodiment of any of the apparatuses, systems, and methods can consist of or consist essentially of—rather than comprise/include/have-any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Some details associated with the embodiments described above and others are described below.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
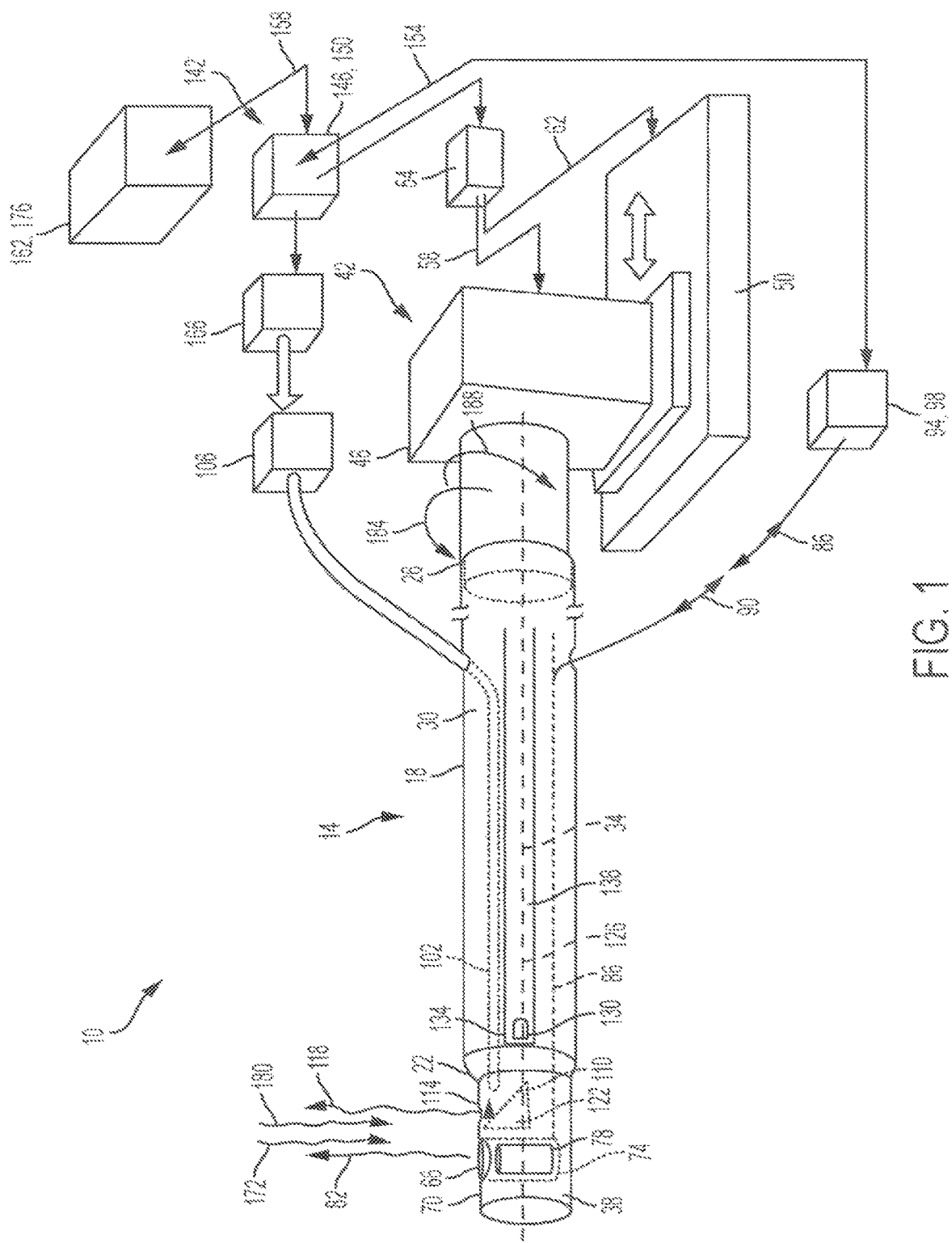
FIG. 1 is a schematic of one embodiment of the present systems.
Figure 2:
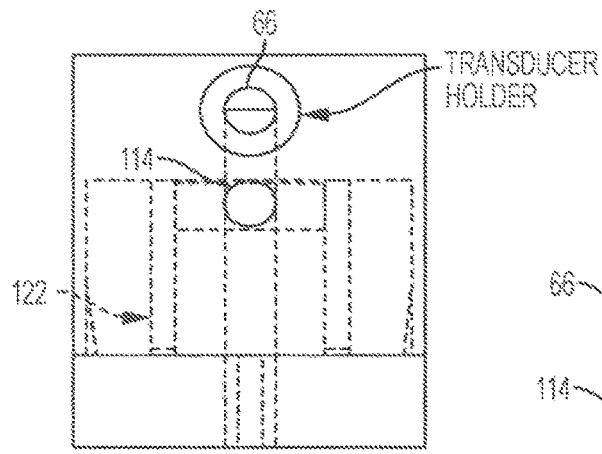
FIGS. 2-5 are first side, second side, third side, and perspective views of one embodiment of an imaging probe of the system of FIG. 1.
Figure 3:
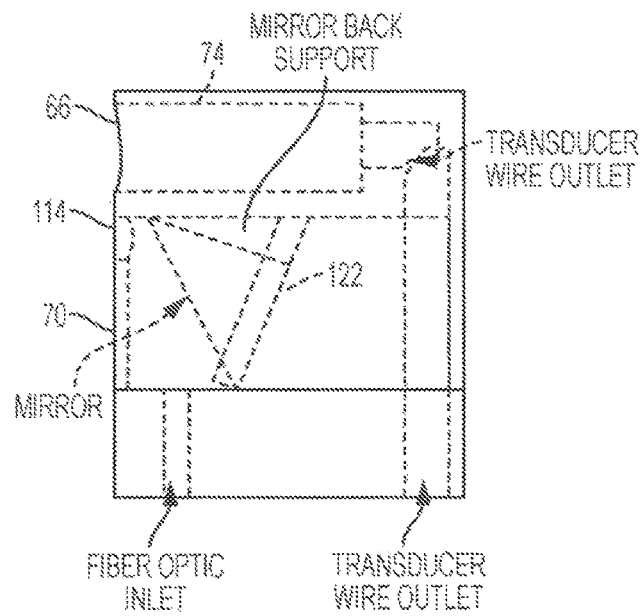
Figure 4:
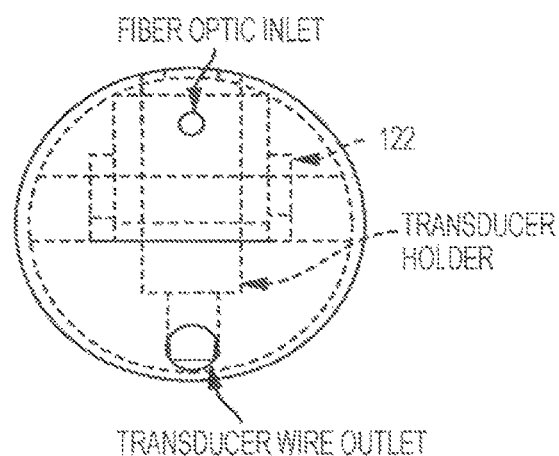
Figure 5:
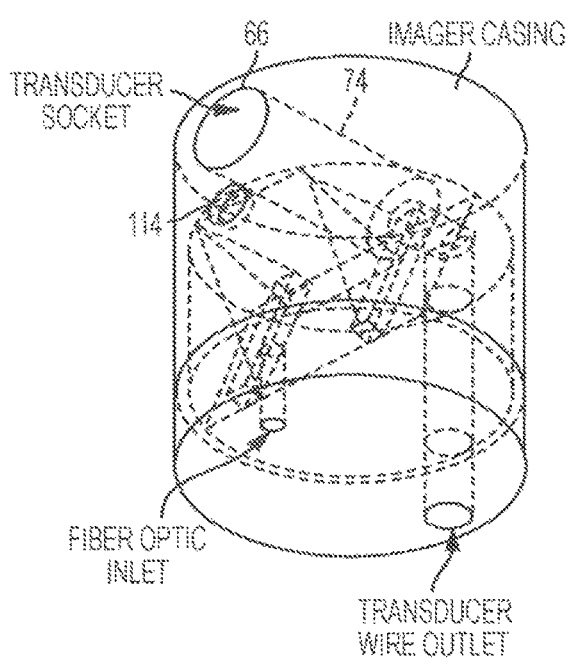

Referring now to the drawings, and more specifically to FIG. 1, shown therein and designated by the reference numeral 10 is one embodiment of the present systems. In the embodiment shown, system 10 includes an insertion device 14. In this embodiment, insertion device 14 may be a biomedical device for screening for (e.g., endometrial, esophageal, prostate, and/or any other solid cancer) cancer by way of imaging and controlled biopsy sample collection.

In the depicted embodiment, insertion device 14 comprises a flexible cannula 18 (e.g., a flexible catheter) having a first end 22, a second end 26, and a channel 30 extending between the first end and the second end. In this embodiment, cannula 18 may be characterized by and described relative to a longitudinal axis 34 extending along a length of the cannula. In the embodiment shown, cannula 18 may be coupled to an imaging probe 38 at first end 22 of the cannula. In some embodiments (e.g., 10), a cannula (e.g., 18) and an imaging probe (e.g., 38) may be integrally formed and/or the imaging probe may be disposed at any position along the cannula between a first end (e.g., 22) and a second end (e.g., 26) of the cannula. In the embodiment shown, second end 26 of cannula 18 may be coupled to an actuator 42. In this embodiment, actuator 42 is configured to be disposed externally relative to a patient during an imaging and/or biopsy sample collection procedure. In this embodiment, actuator 42 includes a rotary motor 46 and a linear actuator 50. For example, in the depicted embodiment, rotary motor 46 may be actuatable to move (e.g., rotate) insertion device 14 about longitudinal axis 34 and linear actuator 50 may be actuatable to move the insertion device axially relative to the longitudinal axis. In this embodiment, actuator 42 may be configured to be (e.g., electronically) coupled to a position control device 54 configured to control the rotational and/or linear velocity, acceleration, and/or position of insertion device 14 relative to the tissue of an organ of a patient. More specifically, in the depicted embodiment, position control device 54 may be configured to send respective (e.g., electronic) signals 58, 62 to rotary motor 46 and/or linear actuator 50 to control the velocity, acceleration, position, and/or the like of insertion device 14.

In the depicted embodiment, imaging probe 38 may include a transducer aperture 66 defined by an outer circumferential surface 70 of the imaging probe. As shown, imaging probe 38 may include a transducer chamber 74 at least partially axially aligned with transducer aperture 66, where the transducer chamber is configured to support an ultrasound transducer 78. In this embodiment, ultrasound transducer 78, when disposed in transducer chamber 74, may be configured to emit an ultrasound signal 82 radially outward (e.g., relative to longitudinal axis 34) through transducer aperture 66. More specifically, in the depicted embodiment, ultrasound transducer 78 may be configured to emit ultrasound signal 82 in a direction substantially perpendicular relative to longitudinal axis 34. In the embodiment shown, insertion device 14 may include an ultrasound transmission line 86 configured to transmit a (e.g., electronic) signal 90 between ultrasound transducer 78 and an ultrasound pulser-receiver 94. As shown, at least a portion of ultrasound transmission line 86 may extend within channel 30 of cannula 18. In the depicted embodiment, ultrasound pulser-receiver 94 may be coupled to an amplifier 98 configured to amplify electronic signal 90 received by the pulser-receiver from transducer 78. In some embodiments, a system (e.g., 10) may include a pulser and a receiver as separate components.

In the depicted embodiment, insertion device 14 may include a light transmission line 102 configured to transmit light from a fiber optic alignment stage 106 to a reflective surface 110, such as, for example, a mirror. As shown, at least a portion of light transmission line 102 may extend within channel 30 of cannula 18. In this embodiment, light transmission line 102 comprises a fiber optic cable. In the embodiment shown, reflective surface 110 may be disposed in imaging probe 38 such that the reflective surface is configured to direct light through a light aperture 114 defined by the imaging probe. More particularly, as shown, reflective surface 110 may comprise a right-angle mirror configured to direct a light signal 118 in a direction substantially perpendicular to longitudinal axis 34. In the depicted embodiment, reflective surface 110 may be coupled to one or more adjustable rail(s) 122 configured to adjust the position of the reflective surface in imaging probe 38 such that the reflective surface reflects light signal 118 through light aperture 114 (e.g., in a direction substantially parallel relative to ultrasound signal). For example, in this embodiment, ultrasound signal 82 emitted by ultrasound transducer 78 and light signal 118 transmitted by light transmission line 102 (e.g., via reflective surface 110) may be configured to be emitted in a direction substantially parallel relative to each other. More specifically, in the embodiment shown, transducer aperture 66 and light aperture 114 may be configured to be substantially longitudinally aligned in imaging probe 38.

In the embodiment shown, insertion device 14 may include a biopsy device 126 removably insertable in cannula 18 and configured to collect a tissue sample from an organ of a patient. In this embodiment, biopsy device 126 comprises a biopsy pipelle. In other embodiments, a biopsy device (e.g., 126) may include any other suitable device configured to collect and/or examine tissue from a patient, such as, for example, a Novak curette and/or the like. As shown, biopsy device 126 may be at least partially disposed in channel 30 of cannula 18 and may include an aperture 130 (e.g., at an end 134 of the biopsy device). In this embodiment, end 134 of biopsy device 126 may be axially and/or laterally movable relative to longitudinal axis 34 such that the biopsy device may be properly positioned in a patient. In the depicted embodiment, for example, biopsy device 126 may be configured to provide a suction force at aperture 130 in an effort to collect a sample of tissue from a patient. Thereafter, the sample of tissue may be stored in a channel 138 of biopsy device 126 for further examination.

In this embodiment, system 10 may include a data acquisition system 142. In the embodiment shown, data acquisition system 142 may include a data acquisition device 146 and a trigger 150. In the depicted embodiment, data acquisition device 146 may be configured to receive an amplified (e.g., electronic) signal 154 from amplifier 98 and transmit image data 158 to a computer 162 having a display, processor, and memory. More specifically, in this embodiment, data acquisition device 146 may be configured to collect quantitative data from pulser-receiver 94 and transmit quantitative data 158 to computer 162 for further processing. In the depicted embodiment, computer 162 may be configured to construct and/or reconstruct a three-dimensional image (e.g., map) representing the (e.g., soft) tissue and/or vasculature surrounding insertion device 14 in real time based on the quantitative data received from data acquisition device 146. In this way and others, system 10 provides a real-time three-dimensional mapping (e.g., a two-dimensional image of a three-dimensional volume) of an organ from inside the organ. In the embodiment shown, computer 162 may include a physician-guided software program (e.g., an algorithm) configured to identify tissue regions of interest, such as, for example, lesions on endometrium tissue.

As shown, data acquisition system 142 may be coupled to position control device 54 and configured to transmit a (e.g., electronic) signal to the position control device thereby directing the rotational and linear movement of insertion device 14 via the position control device. As shown, trigger 150 of data acquisition system 142 may be coupled to a laser 166 and configured to actuate the laser between an on and off state. In the depicted embodiment, laser 166 may comprise a near-infrared laser.

In operation, in this embodiment, insertion device 14 may be inserted into an organ (e.g., a vagina) of a patient via a biological orifice (e.g., vaginal opening). In the depicted embodiment, when insertion device 14 is positioned in the organ, other components of system 10, including actuator 42, may remain positioned externally relative to the organ and/or the patient. After insertion device 14 is disposed in the organ, actuator 42 (e.g., via signals, 58, 62 from position control device 54) may control movement of the insertion device. For example, in this embodiment, actuator 42 may move insertion device 14 proximate to an area of interest in the organ, whereby the insertion device is at a starting position and ready to begin an imaging procedure. Next, the following steps may be performed and/or repeated (e.g., with alterations) until the area of interest in the organ has been appropriately imaged.

In the embodiment shown, ultrasound pulser-receiver 94 may transmit signal 90 to ultrasound transducer 78 via ultrasound transmission line 86. Next, in the depicted embodiment, ultrasound transducer 78 emits ultrasound signal 82 radially outward relative to longitudinal axis 34 and, thereafter, receives an ultrasound echo signal 172 (e.g., an ultrasound signal reflected by the tissue of the organ). In this embodiment, ultrasound transducer 78 may convert ultrasound echo signal 172 into signal 90, which is transmittable via ultrasound transmission line 86 to ultrasound pulser/receiver 94. Next, in this embodiment, signal 90 may be amplified by amplifier 98 and amplified signal 154 may be transmitted to data acquisition device 146, which may transmit image data 158 to computer 162. In the embodiment shown, computer 162 may render on a display 176 a three-dimensional image in real time based on ultrasound echo signal 172 received by ultrasound transducer 78.

In the embodiment shown, trigger 150 may (e.g., by user input via computer 162) direct laser 166 to emit light signal 118 (e.g., a laser beam) into fiber alignment stage 106, which thereby transmits light signal 118 through light transmission line 102 toward reflective surface 110. Thereafter, light signal 118 reflects off of reflective surface 110 is directed radially outward relative to longitudinal axis 34. As shown, in this embodiment, light signal 118 is reflected off of reflective surface 110 in a direction substantially perpendicular to longitudinal axis 34 and/or substantially parallel to ultrasound signal 82. In the depicted embodiment, light signal 118 may induce a photoacoustic effect in the tissue of the organ exposed to the light signal. In this embodiment, heat from light signal 118 may be absorbed by the tissue and may cause the tissue to expand. In turn, the heat-related tissue expansion due to exposure to light signal 118 may result in a photoacoustic signal 180 (e.g., a soundwave) emitted from the tissue. In this embodiment, ultrasound transducer 78 may receive photoacoustic signal 180 and convert the photoacoustic signal into signal 90, which transmittable via ultrasound transmission line 86. Thereafter, as discussed herein, signal 90 may be ultimately transmitted to computer 162 via ultrasound pulser-receiver 94, amplifier 98, and/or data acquisition device 146. In the embodiment shown, computer 162 may reconstruct and/or update the rendered three-dimensional image on display 176 in real time based on photoacoustic signal 180 and/or ultrasound echo signal 172. More particularly, in the depicted embodiment, the three-dimensional image rendered by computer 162 may comprise one or more overlaid images providing a more comprehensive view of the tissue. For example, in this embodiment, the overlaid images may include an optical image (e.g., for insertion device guidance and surface characterization of tissue, such as, of the endometrium), an ultrasound image (e.g., for characterizing tissue density, such as, within the endometrium and myometrium along with thickness of the endometrial stripe), and a photoacoustic image (e.g., for vasculature mapping). In the embodiment shown, the overlaid images may aid in the identification of potential lesions or other problem areas in the tissue.

In this embodiment, system 10 may be configured to capture three-dimensional images while insertion device 14 moves axially and/or rotationally relative to longitudinal axis 34. For example, in the depicted embodiment, position control device 54 may cause rotary motor 46 to rotate insertion device 14 in a first direction 184 such that ultrasound signal 82 and light signal 118 are repeatedly emitted (e.g., at a predetermined frequency) in controlled pulses until at least a full revolution of the insertion device is achieved and a corresponding three-dimensional image is captured by system 10 as described herein. In this embodiment, after at least the full revolution is achieved, position control device 54 may direct linear actuator 50 to move insertion device 14 axially such that imaging probe 38 may capture images of additional tissue. In the embodiment shown, after insertion device 14 is axially moved by linear actuator 50, rotary motor 46 may rotate the insertion device in a second direction 188 (e.g., an opposite direction relative to first direction 184) and system 10 may capture additional three-dimensional images as described herein. In some embodiments (e.g., 10), a position control device (e.g., 54) may direct an actuator (e.g., 42) to rotate an insertion member (e.g., 14) in a first direction (e.g., 184) and/or a second direction (e.g., 188) before and/or after moving the insertion member axially. Thereafter, axial and/or rotational movement of insertion device 14 may be repeated until a comprehensive three-dimensional image of the tissue is captured. In this embodiment, data acquisition device 146 and/or computer 162 may store spatial coordinates of the data which make up the three-dimensional image on display 176. In the depicted embodiment, using the spatial coordinates from the imaging data corresponding to the tissue of interest identified by the physician-guided software program, position control device 54 may direct actuator 42 to move and orient insertion tool 14 relative to the tissue such that biopsy device 126 may collect a biopsy sample of the tissue of interest. Thereafter, insertion device 14 may be removed from the organ and the tissue sample may be examined.

In these ways and others, areas of interest in the organ may be imaged in real time by system 10 and controlled biopsy samples may be collected from the areas of interest by the system based on the real time images.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

What is claimed is:

1. A device for capturing an image within an organ of a patient, the device comprising:
    a cannula having a first end region, a second end region, and a channel between the first end region and the second end region defining a longitudinal axis of the device;
    an imaging probe configured to be coupled to the first end region of the cannula and configured to capture an ultrasound return signal and a photoacoustic signal, the imaging probe comprising:
        a probe body including a first radial aperture and a separate second radial aperture at least partially circumferentially aligned with the first radial aperture,
        a first chamber in the probe body at least partially axially aligned with the first radial aperture,
        a transducer disposed within the first chamber of the probe body and at least partially axially aligned with the first radial aperture, a second chamber within the probe body separate from the first chamber and at least partially axially aligned with the second radial aperture, and a reflective surface disposed within the second chamber of the probe body and at least partially axially aligned with the second radial aperture, wherein the reflective surface is coupled to a rail within the cannula and a position of the reflective surface along the rail is adjustable, wherein the reflective surface is configured to redirect a light signal through the second radial aperture; and a biopsy device coupled to and extending within the cannula, wherein the biopsy device is configured to collect a tissue sample from within the organ;

a light transmission line extending from the second end region, through the cannula, and into the probe body;

a laser disposed proximate the second end region of the cannula and configured to emit the light signal through the light transmission line and through the second radial aperture using the reflective surface, wherein a direction of the light signal is adjustable based on the position of the reflective surface along the rail;

an ultrasound transmission line extending from the second end region, through the cannula, and into the probe body;

a pulser disposed proximate the second end region of the cannula and configured to actuate the transducer via the ultrasound transmission line to emit an ultrasound signal through the first radial aperture;

a computer configured to:
  generate an ultrasound image based on the ultrasound return signal received by the transducer in response to the ultrasound signal,
  generate a photoacoustic image based on the photoacoustic signal received by the transducer in response to the light signal,
  overlay the ultrasound image and the photoacoustic image to construct an overlaid image of the organ in the patient in real time, and
  identify a location of interest based on the overlaid image of the organ; and an actuator coupled to the second end region of the cannula and configured to automatically move the cannula to align the biopsy device to the location of interest based on the overlaid image from the imaging probe.

2. The device of claim 1, wherein the position of the reflective surface is rotatable about the rail.

3. The device of claim 1, wherein the position of the reflective surface is translatable along the rail.

4. The device of claim 1, wherein the probe body further comprises an ultrasound transmission channel communicating between the first chamber and an exterior surface of the probe body.

5. The device of claim 4, wherein the ultrasound transmission line extending from the second end region, through the first end region, and to the ultrasound transmission channel to communicate with the first chamber.

6. The device of claim 5, wherein the transducer is configured to:
  receive an actuation signal via the ultrasound transmission line;
  emit the ultrasound signal through the first radial aperture in response to the actuation signal; receive an ultrasound return signal in response to the ultrasound signal; and transmit an electrical signal via the ultrasound transmission line based on the ultrasound return signal.

7. The device of claim 6, wherein the probe body further comprises a light transmission channel communicating between the second chamber and an exterior surface of the probe body.

8. The device of claim 7, wherein the light transmission line extending from the second end region, through the first end region, and to the light transmission channel to communicate with the second chamber.

9. The device of claim 8, wherein the reflective surface is configured to receive the light signal via the light transmission line.

10. The device of claim 9, wherein the transducer is configured to receive the photoacoustic signal in response to the light signal and transmit an electrical signal via the ultrasound transmission line based on the photoacoustic signal.

11. The device of claim 10, wherein the light transmission light comprises a fiber optic cable.

12. The device of claim 1, wherein the imaging probe and the first end region of the cannula are configured for insertion into the organ of the patient during imaging, and wherein the second end region of the cannula is configured to be disposed externally of the patient during imaging.

13. The device of claim 1, wherein the imaging probe and the cannula are configured to rotate at least one full revolution about the longitudinal axis to capture the ultrasound return signal and the photoacoustic signal.

14. The device of claim 13, wherein the ultrasound return signal and the photoacoustic signal are captured to construct a three-dimensional image from within the organ and comprises at least the ultrasound image and the photoacoustic image.

15. The device of claim 1, wherein the biopsy device rotatable with respect to the cannula.

16. The device of claim 1, wherein the biopsy device is axially and laterally movable with respect to the cannula.

17. The device of claim 1, wherein the biopsy device is selected from the group consisting of a pipelle and a Novak curette.

18. An imaging and biopsy device, comprising:
  a cannula having a first end region, a second end region and a length therebetween;
  an imaging probe having a longitudinal axis and coupled to the first end region of the cannula; and
  a biopsy device at least partially disposed within the cannula;
  wherein the imaging probe comprises:
    an outer surface having a first aperture and a separate second aperture, wherein the first and second apertures are aligned along the longitudinal axis;
    a first chamber at least partially aligned with the first aperture;
    a second chamber separate from the first chamber at least partially aligned with the second aperture;
    a transducer disposed within the first chamber and configured to both emit ultrasound signal and to receive at least one of an ultrasound echo signal and a photoacoustic signal through the first aperture; and
    a reflective surface disposed within the second chamber and configured to redirect a light signal through the second aperture, wherein the reflective surface is coupled to a rail within the cannula and a position of the reflective surface along the rail is adjustable;

a light transmission line extending from the second end region, through the cannula, and into the second chamber of the imaging probe;

a laser disposed proximate the second end region of the cannula and configured to emit the light signal through the light transmission line and through the second radial aperture using the reflective surface, wherein a direction of the light signal is adjustable based on the position of the reflective surface along the rail;

an ultrasound transmission line extending from the second end region, through the cannula, and into the first chamber of the imaging probe;

a pulser disposed proximate the second end region of the cannula and configured to actuate the transducer via the ultrasound transmission line to emit an ultrasound signal through the first radial aperture;

an actuator coupled to the second end region of the cannula and configured to automatically move the cannula to align the biopsy device to a location of interest based on an image based on at least one of the ultrasound echo signal and the photoacoustic signal from the imaging probe.

* * * * *